US009279753B2

(12) United States Patent
Espinosa et al.

(10) Patent No.: US 9,279,753 B2
(45) Date of Patent: Mar. 8, 2016

(54) MICROELECTROMECHANICAL DEVICE AND SYSTEM

(75) Inventors: Horacio Dante Espinosa, Winnetka, IL (US); Rodrigo A. Bernal Montoya, Evanston, IL (US)

(73) Assignee: Northwestern University, Evanston, IL (US)

( * ) Notice: Subject to any disclaimer, the term of this patent is extended or adjusted under 35 U.S.C. 154(b) by 960 days.

(21) Appl. No.: 13/506,103

(22) Filed: Mar. 27, 2012

(65) Prior Publication Data

US 2012/0297897 A1 Nov. 29, 2012

Related U.S. Application Data

(63) Continuation of application No. PCT/US2010/002819, filed on Oct. 22, 2010.

(60) Provisional application No. 61/279,833, filed on Oct. 26, 2009.

(51) Int. Cl.
*G01N 3/08* (2006.01)

(52) U.S. Cl.
CPC ............ *G01N 3/08* (2013.01); *G01N 2203/005* (2013.01); *G01N 2203/0286* (2013.01)

(58) Field of Classification Search
CPC ....................................................... G01N 3/08
USPC ......................................................... 324/715
See application file for complete search history.

(56) References Cited

U.S. PATENT DOCUMENTS

| 4,335,350 | A * | 6/1982 | Chen | 324/716 |
|---|---|---|---|---|
| 6,636,050 | B2 | 10/2003 | Nakayama et al. | 324/537 |
| 6,798,315 | B2 * | 9/2004 | Schaefer | 333/105 |
| 7,586,105 | B2 | 9/2009 | Molhave | 250/440.11 |
| 8,438,660 | B2 * | 5/2013 | Hirooka et al. | 850/9 |
| 2001/0043023 | A1 * | 11/2001 | Jerman et al. | 310/309 |
| 2006/0164194 | A1 | 7/2006 | Deligianni et al. | 335/78 |
| 2009/0219047 | A1 | 9/2009 | Petersen et al. | 324/755.05 |

OTHER PUBLICATIONS

Espinosa et al., Design and operation of a MEMS-based material testing system for nanomechanical characterization, Journal of Microelectromechanical Systems, vol. 16, No. 5, Oct. 2007, pp. 1219-1231.

Zhu et al., An electromechanical material testing system for in situ electron microscopy and applications, Proceedings of the National Academy of Sciences of the United States of America, 2005, vol. 102, No. 41, Oct. 11, 2005, pp. 14503-14508.

* cited by examiner

*Primary Examiner* — Jeff Natalini

(57) ABSTRACT

A microelectromechanical device for electromechanical testing a specimen having a nano-scale dimension is formed on a multi-layered semiconductor substrate (chip) and includes an electrothermal or electrostatic actuator for applying a displacement load (force) to the specimen, a load sensor for sensing the load (force) experienced by the specimen. The specimen is disposed between first and second movable shuttles of the actuator and load sensor, which shuttles comprise electrically insulating layers so as to electrically isolate the shuttles and specimen from the actuator and the load sensor on the substrate. A four-terminal Kelvin array is provided to provide specimen electrical characterization measurements and includes first and second outer terminals connected to a current source and to opposite end locations of the specimen and first and second inner terminals connected to a high input impedance voltage meter and to the specimen at other locations between the first and second outer terminals.

14 Claims, 4 Drawing Sheets

MICROELECTROMECHANICAL DEVICE AND SYSTEM

RELATED APPLICATION

This application is a continuation of international PCT application No. PCT/US2010/002819 filed Oct. 22, 2010, which claims benefits and priority of United States provisional application Ser. No. 61/279,833 filed Oct. 26, 2009, the disclosure of which is incorporated herein by reference.

CONTRACTUAL ORIGIN OF THE INVENTION

This invention was made with government support under Grant No. N00014 08-1-0108 awarded by the Office of Naval Research (ONR). The Government has certain rights in the invention.

FIELD OF THE INVENTION

The present invention provides a microelectromechanical device and system for characterizing the electrical and mechanical properties of a nanostructure, such as a carbon nanotube, nanowire, nanoscale film, molecule, and the like.

BACKGROUND OF THE INVENTION

Nanostructures, such as carbon nanotubes and nanowires, have been used in broad applications ranging from nanocomposites to nanoelectromechanical systems (NEMS).

Characterization of electrical transport properties of nanostructures can be carried out using various metrics. One of the most frequently used is resistivity, which measures the current response of the nanostructure with an applied voltage or vice-versa. Two direct methods exist for this characterization, namely, two-terminal and four-terminal-Kelvin characterization.

Reports of two and four-contact measurements of resistivity exist for many nanostructures, in particular for nanowires. In the two-terminal technique, an electrical contact is made on each end of a slender specimen. By making current (I) flow from one end to the other, and measuring the voltage (V) developed across the terminals, for various values of the current, the equivalent resistance of the nanostructure can be obtained from the slope of the V vs. I curve. From this, the resistivity of the nanostructure can be obtained from its geometry. Alternatively, the same can be done by applying a voltage and measuring the current.

However, this method has a caveat; namely, no matter the way the contacts are made, there is an associated resistance (Rc) to them. As a result, the test current (I) will make appear a potential difference across them (Vc), which adds to the actual potential difference in the nanostructure (Vn). However, because the measurement is recording the total potential difference (V), the slope of a V vs. I curve will reveal the resistance of the specimen plus contacts, not just the one of the specimen. As a conclusion it can be said that the measurement will reflect the true properties of the nanostructure (Rn) only if the resistance of the contacts is very close to zero or very small compared to the resistance of the nanostructure (Rc<<Rn).

Unfortunately, because contacts to nanostructures are complex and difficult, this condition is hardly ever fulfilled. In many cases the contact is made through electron-beam-induced deposition (EBID) of platinum (Pt) or Ion-beam induced deposition (IBID) of the same metal. However, because these depositions have a relatively large percentage of amorphous carbon [reference 5], the resistance of this deposition is large compared to that of pure platinum and consequently cannot be ignored. On other cases, contact is made through metal electrodes, such as gold [reference 6]. This can be advantageous if the specimen has a similar work function to that of the metal electrode, but that is not always the case, resulting in formation of non-ohmic contacts.

An object of the present invention is to employ the four-terminal Kelvin technique in a microelectromechanical device (MEMD) or system (MEMS) to eliminate any influence of the contacts in the measurement. In this technique, a current is injected into the specimen through two contacts made in the outermost ends of the sample. In between these two contacts, another pair of terminals is connected and the voltage developed across them is measured. Because the measurement of voltage relies on an instrument with very high input impedance, the current flowing through the voltage meter will be almost zero. Thus, the influence of the resistance of the contacts is eliminated because no matter their value, the slope of the curve of V vs. I will always be the resistance of the portion of the specimen between the inner terminals.

SUMMARY OF THE INVENTION

The present invention involves a micro-electromechanical device incorporating four-terminal-Kelvin electrical characterization capability of nanostructures, coupled with mechanical testing and, optionally, simultaneous imaging inside a transmission electron microscopy (TEM) (in-situ TEM). The device allows the testing of nanostructures such as carbon nanotubes (CNT), nanowires (nW), nanoscale thin films such as graphene layers, biological molecules (e.g. proteins and DNA), and the like. Electrical characterization of the specimen can include, but is not limited to, characterization of piezoelectric and piezoresistive properties of the specimen.

An illustrative embodiment of the invention involves a microelectromechanical device that is disposed on a multi-layered substrate to electromechanically-test a specimen having a nano-scale dimension wherein the device comprises a movable actuator shuttle comprising an electrically insulating layer, a movable load sensor shuttle comprising an electrically insulating layer and spaced apart from the actuator shuttle for receiving a specimen therebetween for testing and electrically isolating the specimen, and a four-terminal array having first and second outer electrical terminals connected to spaced-apart locations of the specimen and first and second inner electrical terminals connected to the specimen at other locations between the first and second outer terminal electrodes.

A microelectromechanical system pursuant to the invention connects the first and second outer metallic terminals to a current source and to opposite outer (e.g. near end) locations of the specimen to supply current thereto and connects the first and second inner metallic terminals to a high input impedance voltage meter and to the specimen at locations between the first and second outer terminal electrodes.

The specimen can be subjected to a tensile displacement or compressive displacement with suitable actuator modifications. The four-terminal array is provided for electrical characterization of the specimen during mechanical testing.

Practice of the present invention is advantageous in providing capability of four-terminal Kelvin electrical characterization that allows ultimate certainty about the electrical transport properties of the nanostructure. This is a result of eliminating the influence of the nanostructure/contact-electrode interface on the measurement of properties. In short, it allows to test the true electrical properties of a nanostructure instead of the properties of the nanostructure/contacts composite specimen. This, in addition to the mechanical-testing capabilities, results in a system of unprecedented capabilities for mechanical and electrical testing of nanostructures.

Other advantages of the present invention will become apparent from the following detailed description of the invention taken with the following drawings.

DETAILED DESCRIPTION OF THE INVENTION

The present invention described herein provides a microelectromechanical device (MEMD) fabricated by surface micromachining on a multi-layered semiconductor substrate (e.g. silicon substrate or chip) for electrical and mechanical characterization (testing) of a specimen having a nano-scale dimension. The device can be used to test a nanostructure such as carbon nanotube (CNT), nanowire (NW) and nanoscale thin film such as a graphene layer having a nano-scale dimension, which is 200 nm or less (such as specimens having a dimension from 100-200 nm can be tested). For example, for a CNT, the nano-scale dimension can be the CNT diameter and/or the CNT length. For a NW, the nano-scale dimension can be the NW diameter and/or the NW length. For a thin film, the nano-scale dimension typically is the film thickness which is less than 100 nm.

Figure 1A:
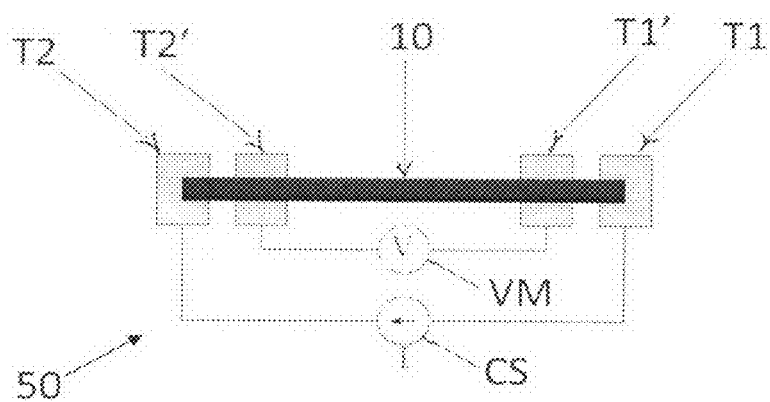
FIG. 1a is a schematic of the four-terminal Kelvin technique. Four contacts are made to the specimen, a current is injected through the outer terminals and the developed voltage is measured in the inner terminals.
Figure 1B:
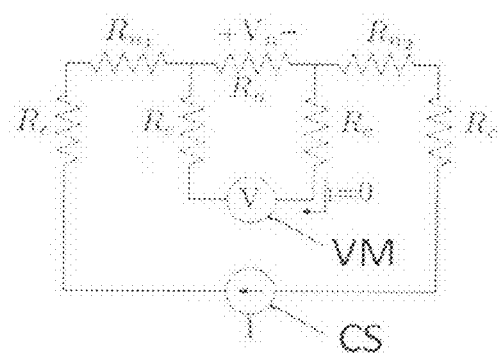
FIG. 1b shows the equivalent circuit. Note that no matter the values of Rc, Rn1, Rn2, the slope of a curve V Vs. I will be Rn, which is the resistance of the portion of the nanostructure between the inner terminals.

Pursuant to the present invention, the microelectromechanical device (MEMD) incorporates four-terminal Kelvin electrical characterization (specimen piezoelectric and piezoresistive properties) capability of a nanostructure coupled with mechanical testing (e.g. specimen Young's modulus, failure strength, stress-strain properties) and optionally simultaneous imaging inside a transmission electron microscopy (TEM) (in-situ TEM). A four-terminal Kelvin array is shown in Figure 1a, while the equivalent electrical circuit of the four-terminal Kelvin array is shown in FIG. 1b for purposes of illustration.

For purposes of illustration and not limitation, the MEMD is described herebelow with respect to a microelectromechanical tensile testing system, although the invention is not so limited as will become apparent. The microelectromechanical tensile testing system allows application of controlled uniaxial displacement to an elongated specimen 10, see FIGS. 2 and 3.

Referring to FIGS. 2, 4 and 5a-5c, the microelectromechanical device is formed as multiple layers on a substrate 100, such as a silicon substrate (chip) and includes an actuator 20 having an actuator shuttle 21 (first shuttle) for applying a displacement force to a specimen and a load sensor 40 having a load sensor shuttle 41 (second shuttle) for sensing the displacement experienced by the specimen 10, which displacement is used to determine the load (force) applied to the specimen. The movable shuttles 21, 41 are made of electrically insulating layers to electrically isolate the specimen 10 from the actuator 20 and the load sensor 40, although the shuttle layers 21, 41 are rigidly and integrally connected to the conductive shuttle 21' of actuator 20 and the conductive shuttle 41' of the load sensor 40, respectively, FIGS. 4 and 5b-5c, so as to move in response to actuator movement.

Figure 5A:
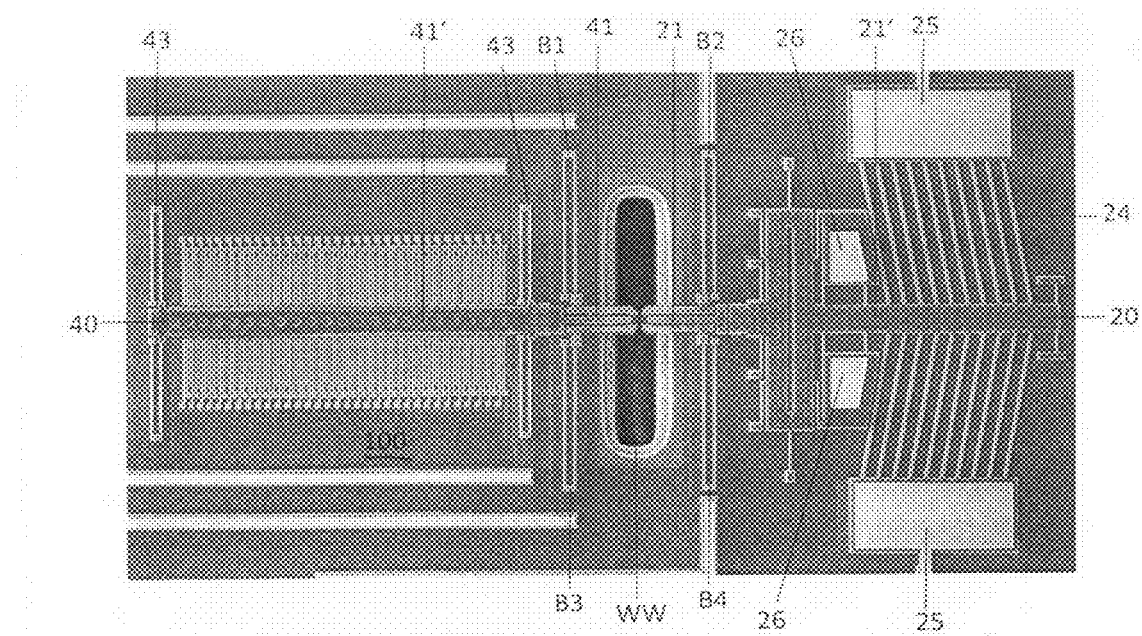
FIG. 5a is a scanning electron microscope image of a MEMD pursuant to the invention where the load sensor and electrothermal actuator are shown.
Figure 5B:
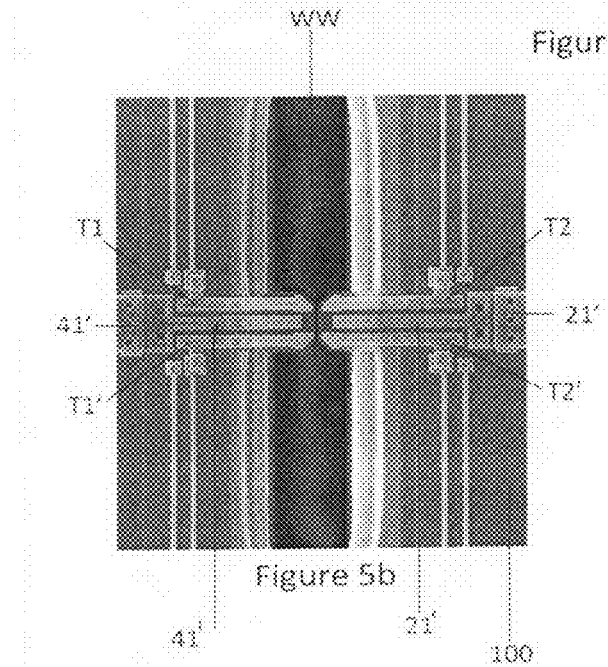
FIG. 5b and FIG. 5c are scanning electron microscope images at greater magnification of the actuator and load sensor shuttles of the MEMD.

The actuator 20 can comprise an electrothermal actuator based on the thermal expansion of freestanding V-shaped beams 24 when subjected to Joule heating, FIG. 5a. The freestanding V-shaped beams are supported at one end for axial motion by axially extending stationary heat sink stationary anchors 25 and are connected at the other end to the actuator shuttle 21', which is moved axially by beam motion. For purposes of illustration and not limitation, the V-shaped beams (300 microns long, 8 microns wide, 3.5 microns thick) are connected to and suspended from two pairs of anchors 25 (320 microns long, 155 microns wide, and 2 to 3.5 microns thick). Additional heat sink anchors 26 connect to actuator shuttle 21' to reduce the temperature of actuator-specimen interface. The beam angle of inclination can be 10 to 30 degrees. Such a thermal actuator is described in detail in references [1], [7], and [8] listed below, the teachings of which are incorporated herein by reference to this end.

Pursuant to the present invention, the thermal actuator 20 is not in direct electrical contact with the specimen 10 as in the references [1], [7], and [8] and instead is electrically insulated therefrom by inner actuator shuttle 21 which comprises an electrically insulating layer integrally connected to outer conductive actuator shuttle 21', FIGS. 4 and 5c, as described in more detail below. The conductive actuator shuttle 21' is shown having an integral T-shaped extension overlying the insulating shuttle 21, FIGS. 5b, 5c. The thermal actuator is displacement controlled which is useful in testing relatively stiff and brittle specimens (e.g. nanowires or ultrathin films).

In an alternate embodiment, an electrostatic actuator (comb drive) can be used to cause displacement of the specimen. When used, the comb drive actuator is force-controlled and suitable for testing relatively compliant specimens, such as CNT's. The comb drive actuator also is described in references [1], [7], and [8]. However, pursuant to the present invention, the comb drive actuator, when used, is not in direct electrical contact with the specimen 10 as in the references and instead is electrically insulated therefrom as described in more detail below.

The load sensor 40 is employed to electronically sense the displacement experienced by the specimen 10, which displacement is used with load sensor stiffness to determine the applied specimen load with nano-Newton resolution. For purposes of illustration and not limitation, the load sensor 40 can be based on differential capacitive sensing. The load sensor measures the load (force) that is applied to the specimen 10 by actuator 20. The load sensor comprises one set of moving electrodes (fingers) connected to an outer load sensor shuttle 41' and two sets of stationary electrodes (fingers), FIG. 5a. For purposes of illustration and not limitation, the moving fingers can be 107 microns long, 4 microns wide, 2 microns thick. The stationary fingers can have similar dimensions. The conductive load sensor shuttle 41' is shown having an integral T-shaped extension overlying the insulating shuttle 41, FIGS. 5b, 5c.

The outer load sensor shuttle 41' is supported by two pairs of arc-like folded beams 43. One pair of much more compliant folded beams (B1 and B3) close to the specimen support the insulating shuttle 41, FIG. 5a. The displacement of the movable fingers is equal to the axial deflection of the actuator V-shaped inclined beams (to be described below) minus the specimen displacement. Through calibration of the load sensor stiffness, the load can be computed as described in references [1], [7], and [8], which are incorporated herein by reference to this end. Capacitance measurements can be made using charge sensing circuit (Capacitive Readout MS3110 CMOS chip available from Microsensors, Costa Mesa, Calif.) which detects the capacitance change at attofard level and is described, along with the capacitive load sensor, in references [1], [7], and [8] listed below incorporated herein by reference. The capacitive sensing circuit can be disposed on the same substrate as the MEMD or on a different chip in a two-part chip system.

Pursuant to the present invention, the capacitive load sensor 40 is not in direct electrical contact with the specimen 10 as in the references [1], [7], and [8] and instead is electrically insulated therefrom by inner load sensor shuttle 41 which comprises an electrically insulating layer integrally connected to the outer conductive load sensor shuttle 41' as described in more detail below in practice of the invention.

The inner actuator shuttle 21 and the inner load sensor shuttle 41 are made of electrically insulating layers (e.g. silicon nitride) to electrically isolate the specimen 10 from the actuator 20 and the load sensor 40. For example, the inner, insulating actuator shuttle 21 is connected integrally by layer deposition during device poly-MUMPS fabrication with the outer conductive actuator shuttle 21' so to transmit load (force) to the specimen 10 in response to actuator motion. Similarly, the inner insulating shuttle 41 of the load sensor 40 is connected integrally by layer deposition during device fabrication with the outer conductive load sensor shuttle 41' so to transmit displacement of the specimen 10 to the load sensor 40. For purposes of illustration and not limitation, the inner insulating actuator shuttle 21 can have a length of 120 microns, width of 65 microns and thickness of 0.8 microns. The inner insulating load sensor shuttle 41 can have a length of 120 microns, width of 65 microns and thickness of 0.8 microns.

Figure 4:
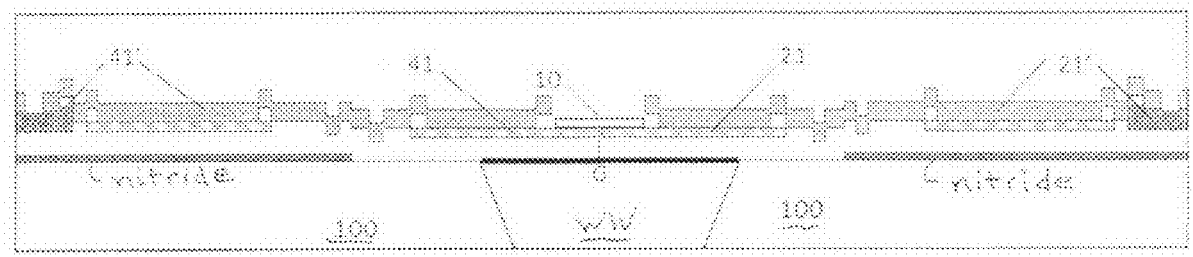
FIG. 4 is a sectional view along the longitudinal centerline of the actuator and load sensor shuttles of the microelectromechancial device (MEMD) of the invention showing silicon nitride layers forming the insulating inner shuttles.
Figure 5C:
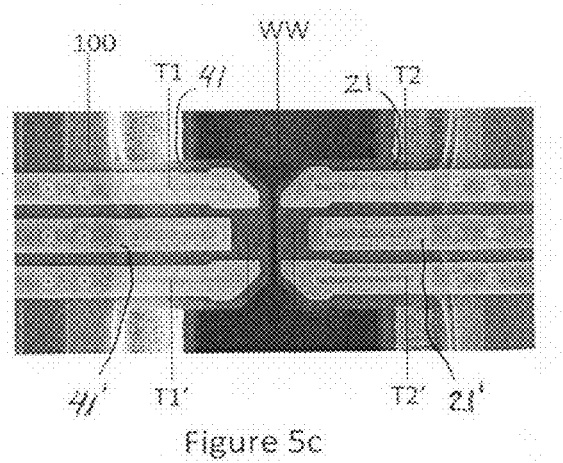

The specimen 10 is disposed across the gap G spanning across the facing ends of the inner electrically insulating actuator shuttle 21 and the inner load sensor shuttle 41, FIG. 4. The gap can be 2000 nm or less in width. The shuttles 21, 41 are formed of the above described electrically insulating shuttle layers so as to electrically isolate the inner shuttles 21, 41 and thus specimen 10 thereon from the actuator and the load sensor. The insulating layers for the inner shuttles 21, 41 are shown in FIG. 4 and can comprise silicon nitride (e.g. $Si_3N_4$) for purposes of illustration and not limitation since other insulating materials can be employed to form the electrically insulating shuttle layers.

The two ends of the slender specimen 10 are joined to the inner electrically insulating shuttles 21, 41. Actuator shuttle 21, 21' of thermal actuator 20 can impose a controlled displacement on the specimen 10, therefore straining the specimen 10. The load sensor shuttle 41, 41' allows measurement of the displacement experienced by the specimen, which displacement is used to determine load (force) applied to the specimen. Below the area were the specimen is tested, there is an optional opening or TEM window WW which allows observation of the sample in the TEM (see references [1], [7], and [8].

Fabrication of the MEMD structural layered features on the substrate can be conducted using nitride patterning and standard poly-MUMPS fabrication as described in references {1], [7], and [8] wherein electrically conductive doped silicon layers and electrically insulating oxide layers are deposited/ etched to build up the MEMD nanostructural features. Fabrication of the MEMD can be obtained commercially available from MEMSCAP Inc. of Durham, N.C. or any other commercial MEMS foundry (e.g. SUMMIT V from Sandia National Lab). In order to provide the window WW, FIGS. 4 and 5a-5c, for in-situ TEM testing, the poly-MUMPS fabrication process is modified to provide for backside grinding and photoresist patterning, deep reactive ion etching (DRIE) to etch the window, and a device release step. In the event the MEMS is to be used for SEM, AFM, and X-ray testing, the standard poly-MUMPS fabrication can be employed since no window is needed.

Figure 3:
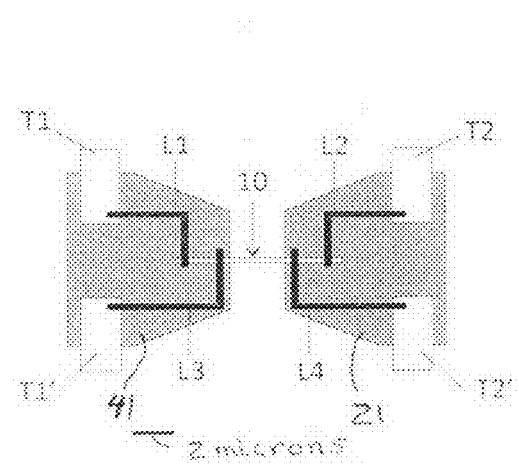
FIG. 3 is an enlarged schematic view of the actuator and load sensor shuttles made of electrical insulating material ($Si_3N_4$) and four-terminal-Kelvin measurement features.

The specimen 10 can be fastened between the inner insulating shuttles 21, 41 by various techniques. For example, referring to FIG. 3, a specimen 10 is shown having its opposite ends attached to the inner shuttles 21, 41 by EBID of platinum (Pt) that forms Pt extensions L1, L2, L3, L4 of conductive polysilicon folding beams B1, B2, B3, B4. The Pt can be deposited onto the opposite specimen ends and adjacent shuttle surfaces to weld the specimen in place and connect to the conductive folding beams as shown in FIG. 3. EBID can be conducted in any Scanning Electron Microscope (SEM) or Focused Ion Beam (FIB) system with capabilities of metal deposition. For purposes of illustration and not limitation EBID of platinum is shown, but other electrically conductive materials can be employed to form the electrically conductive specimen grips, for example tungsten. A conventional nanomanipulator (Klockle Nanotechnik, Aachen, Germany) can be used to place the specimen onto the shuttles 21, 41. Alternately, the specimen, especially a thin film specimen, can be formed integrally on the inner shuttles 21, 41 by deposition of the thin film directly onto the shuttles 21, 41.

Figure 2:
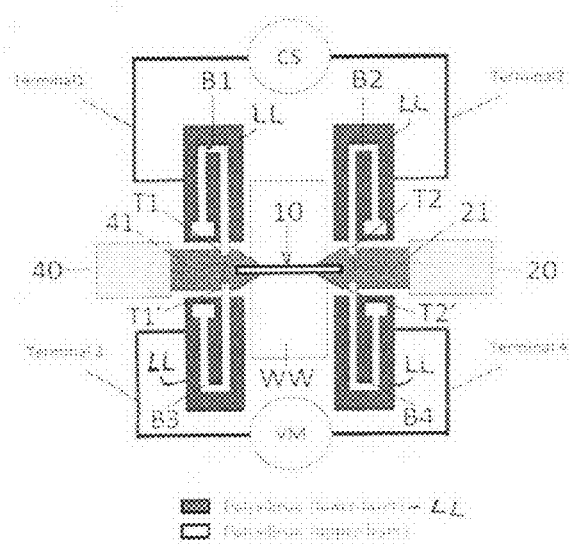
FIG. 2 is a schematic view of the microelectromechanical system (MEMS) pursuant to an embodiment of the invention.

Pursuant to the invention, a four-terminal Kelvin array 50 is provided to contact the specimen and comprises first and second outer electrically conductive terminals T1, T2 connected to a current source CS and to opposite end locations of the specimen 10 and first and second inner electrically conductive terminals T1', T2' connected to a high input impedance voltage meter VM and to the specimen at other locations between the first and second outer terminal T1, T2, FIGS. 1a, 2 and 3. The four-terminal Kelvin array enables electrical properties testing (e.g. specimen piezoelectric and piezoresistivity properties).

The outer conductive terminals T1, T2 can comprise doped polysilicon layers deposited in the poly-MUMPS process so as to form respective folding beams B1, B2 as described below, which are connected to different electrically conductive (polysilicon) layers of the multi-layered substrate 100, which in turn are connected to current source CS, FIGS. 1a and 2, of the MEMS via the exterior terminals 1 and 2 on the substrate 100, FIG. 2.

The inner conductive terminals T1', T2' likewise can comprise doped polysilicon layers deposited in the poly-MUMPS process so as to form respective folding beams B3, B4 connected to other different electrically conductive (polysilicon) layers of the multi-layered substrate 100, which in turn are connected to a high input impedance voltage meter, such as a Keithley 4200 voltage meter available from Keithley Instruments, FIGS. 1a and 2, of the MEMS via exterior terminals 3 and 4 on the substrate 100, FIG. 2.

In particular, in order to accomplish the four-terminal Kelvin arrangement, four folded doped polysilicon beams are deposited during the poly-MUMPS process so that two folded beams are attached to each inner insulating shuttles 21, 41, FIGS. 2 and 3. Each folded beam B1, B2; B3, B4 is anchored to a different underlying conductive (doped polysilicon) layer of the multi-layered poly-MUMPS processed substrate 100. These four (4) electrically independent conductive (doped polysilicon) folded beams B1, B2; B3, B4 are deposited close to the specimen area on the shuttles 21, 41 effectively having four connections in the vicinities of the specimen 10, FIG. 3. As mentioned, each of these folded beams is anchored to a respective lower layer of electrically conductive, doped polysilicon, which is used, in turn, to make electrical paths from the specimen 10 to the exterior terminals 1, 2, 3, 4 placed on the exterior of the MEMS as illustrated schematically in FIG. 2. The folding beams B1, B2, B3, B4 are flexible enough to accommodate the motion of the shuttles 21, 21'; 41,41' relative to the bordering stationary substrate structure without breaking The four folded beams B1, B2; B3, B4 are electrically connected to the specimen through electron beam induced deposition (EBID) of Pt metal on the ends of the specimen, on the inner insulating shuttles 21, 41 and associated electrical terminals T1, T2; T1', T2' to form respective L-shaped folding beam layer extensions L1, L2; L3, L4, FIG. 3. The four folding beams plus their respective extensions thereby form the four-terminal Kelvin arrangement.

The EBID of the Pt beam extensions L1, L2; L3, L4 on the shuttles 21, 41 can be conducted in any Scanning Electron Microscope (SEM) or Focused Ion Beam (FIB) system with capabilities of metal deposition. For purposes of illustration and not limitation, EBID of platinum is shown, but other electrically conductive materials can be employed to form the electrically conductive beam extensions that also function as specimen grips, for example tungsten. Another possible method of contacting is by using a shadow mask (defining the metal area) and subsequently evaporating a metal film on top of the sample.

In effect, the four folded beams are extended by the respective metallic beam extensions L1, L2; L3, L4 to the specimen by EBID-Pt, which can easily achieve features of less than 100 nm. Note that because the system uses the four-contact-Kelvin method of electrical characterization, the resistance of this platinum deposition is not relevant and does not affect the final result of the characterization of the nanostructure. Furthermore, it allows a fabricator to use the lower-conductivity but less aggressive EBID instead of IBID process. The IBID process produces higher conductivity but is known to introduce structural defects in nanostructure.

By virtue of this four-terminal Kelvin arrangement, the invention provides mechanical testing capabilities while making four independent contacts to the tested nanostructure. Further, when the four terminal contacts are made, it is possible to perform electrical measurements simultaneously with mechanical measurements, this time with the capability of truly probing the specimen electrical properties without any previous characterization of the contacts. Note that because current is injected from the outer terminal electrodes, and voltage is measured in the inner ones, the properties of the specimen can be probed under mechanical deformation.

The MEMD can be fabricated in modified manner to conduct compression testing of the specimen 10. For example the orientation of the inclined (V-shaped) beams of the actuator 20 can be reversed such that motion is toward the load sensor 40. A natural extension of the setup allows the performance of in situ indentation testing. In this setup, a nanowire or CNT having the function of an indenter can be mounted by nanomanipulation on the actuator shuttle 30 and moved toward the load sensor to indent a specimen.

Although the present invention has been described in connection with certain embodiments thereof, those skilled in the art will appreciate that changes and modifications can be made therein without departing from the spirit and scope of the invention as set forth in the appended claims.

REFERENCES, WHICH ARE INCORPORATED HEREIN BY REFERENCE

1. Zhu, Y. and H. D. Espinosa, *An electromechanical material testing system for in situ electron microscopy and applications.* Proceedings of the National Academy of Sciences of the United States of America, 2005. 102(41): p. 14503-14508.
2. He, R. and P. Yang, *Giant piezoresistance effect in silicon nanowires.* Nat Nano, 2006. 1(1): p. 42-46.
3. Boukai, A. I., et al., *Silicon nanowires as efficient thermoelectric materials.* Nature, 2008. 451(7175): p. 168-171
4. Werner, F., et al., *Electrical Conductivity of InN Nanowires and the Influence of the Native Indium Oxide Formed at Their Surface.* Nano Letters, 2009. 9(4) : p. 1567-1571.
5. van Dorp, W. F. and C. W. Hagen, *A critical literature review of focused electron beam induced deposition.* Journal of Applied Physics, 2008. 104(8): p. 081301-42.
6. Xu, S. Y., J. Xu, and M. L. Tian, *A low cost platform for linking transport properties to the structure of nanomaterials.* Nanotechnology, 2006. 17(5): p. 1470-1475.
7. Espinosa, H. D., Y. Zhu, and N. Moldovan, *Design and Operation of a MEMS-Based Material Testing System for Nanomechanical Characterization.* Journal of Microelectromechanical Systems, 2007. 16(5): p. 1219-1231.
8. Zhu, Y., A. Corigliano, and H. D. Espinosa, *A thermal actuator for nanoscale in-situ microscopy testing: design and characterization.* Journal of Micromechanics and Microengineering, 2006. 16(2): p. 242-253.
9. Agrawal, R., et al., *Elasticity Size Effects in ZnO Nanowires—A combined Experimental-Computational Approach.* Nano Letters, 2008. 8(11): p. 3668-3674.

The invention claimed is:

1. A microelectromechanical device formed on a multi-layered substrate for testing a specimen having a nano-scale dimension, comprising an actuator having a movable actuator shuttle comprising an electrically insulating layer, a load sensor having a movable load sensor shuttle comprising an electrically insulating layer and spaced apart from the actuator shuttle for receiving a specimen for testing therebetween, wherein the electrically insulating layer of the actuator shuttle and of the load sensor shuttle receive a respective end region of the specimen thereon for electrically isolating the specimen from said actuator and said load sensor during testing, and a four-terminal array having first and second outer electrical terminals with respective extensions residing on the actuator shuttle and load sensor shuttle and connected to the electrically isolated specimen at spaced apart locations and first and second inner electrical terminals with respective extensions residing on the actuator shuttle and load sensor shuttle and connected to the electrically isolated specimen at other locations between the first and second outer terminals.

2. The device of claim 1 wherein the electrical insulating layer of the actuator shuttle and the load sensor shuttle comprises silicon nitride.

3. The device of claim 1 wherein the first and second outer electrical terminals include a respective electrically conductive terminal extension deposited on the respective actuator shuttle and load sensor shuttle.

4. The device of claim 3 wherein the first and second outer electrical terminals include respective electrically conductive flexible folding seams that are connected to the respective terminal extension to accommodate movement of the actuator shuttle and the load sensor shuttle.

5. The device of claim 1 wherein the first and-second inner electrical terminals include a respective electrically conductive terminal extension deposited on the respective actuator shuttle and load sensor shuttle.

6. The device Of claim 5 wherein the first and second inner electrical terminals include respective electrically conductive flexible folding beams that are connected to the respective terminal extension to accommodate movement of the actuator shuttle and the load sensor shuttle.

7. The device of claim 5 wherein the first and second outer and inner terminals each comprises a nee metal.

8. The device of claim 1 wherein the actuator is displacement controlled or force controlled.

9. The device of claim 1 wherein the load sensor comprises a differential capacitive sensor of displacement.

10. A MEMS comprising the device of claim 1, a current source connected to the outer terminals, and a high input impedance voltage meter connected to the inner terminals.

11. A method of testing a specimen having nano-scale dimension, comprising disposing the specimen between first and second movable, spaced apart shuttles which are formed on a multi-layered substrate and comprise respective electrically insulating layers on which respective regions of the specimen are disposed to electrically isolate the specimen during testing, moving one of the first and second shuttles to uniaxially displace the specimen, sensing displacement of the specimen by sensing displacement of the other of the first and second shuttles, and applying an electrical current to spaced apart locations of the specimen and measuring voltage between other locations residing between the current-supply locations of the specimen using a four-terminal array wherein applying of the electrical current and measuring of the voltage occur concurrently while the electrically isolated specimen is being displaced between the actuator shuttle and the load sensor shuttle.

12. The method of claim 11 wherein the first and second shuttles comprise silicon nitride layers.

13. The method of claim 11 including connecting first and second outer, current-supplying electrical terminals to the specimen via a respective electrical terminal extension disposed on the electrically insulating layer of the respective actuator shuttle and the load sensor shuttle.

14. The method of claim 13 including connecting first and second inner, voltage-sensing electrical terminals to the specimen via a respective electrical terminal extension disposed on the electrically insulating layer of the respective actuator shuttle and the load sensor shuttle.

* * * * *